(12) United States Patent
Casale

(10) Patent No.: US 9,750,464 B2
(45) Date of Patent: Sep. 5, 2017

(54) SYSTEM AND METHOD FOR BLOOD PRESSURE ESTIMATION

(71) Applicant: Stichting IMEC Nederland, Eindhoven (NL)

(72) Inventor: Pierluigi Casale, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 14/969,300

(22) Filed: Dec. 15, 2015

(65) Prior Publication Data

US 2016/0166160 A1 Jun. 16, 2016

(30) Foreign Application Priority Data

Dec. 15, 2014 (EP) .................................. 14197973

(51) Int. Cl.
| | | |
|---|---|---|
| *A61B 5/021* | (2006.01) | |
| *A61B 5/0402* | (2006.01) | |
| *A61B 5/00* | (2006.01) | |
| *A61B 5/0295* | (2006.01) | |

(52) U.S. Cl.
CPC ............ *A61B 5/7278* (2013.01); *A61B 5/021* (2013.01); *A61B 5/0295* (2013.01); *A61B 5/7253* (2013.01); *A61B 5/7267* (2013.01)

(58) Field of Classification Search
None
See application file for complete search history.

(56) References Cited

U.S. PATENT DOCUMENTS

| | | | | |
|---|---|---|---|---|
| 8,620,591 B2 * | 12/2013 | Wegerich | ............ | A61B 5/0205 600/301 |
| 2008/0214942 A1 * | 9/2008 | Oh | ...................... | A61B 5/02125 600/485 |
| 2011/0245628 A1 * | 10/2011 | Baker, Jr. | ............. | A61B 5/0205 600/301 |

OTHER PUBLICATIONS

Gesche, Heiko et al., "Continuous Blood Pressure Measurement by Using the Pulse Transit Time: Comparison to a Cuff-Based Method", Eur. J. Appl. Physiol., May 10, 2011, pp. 7 pages.

(Continued)

*Primary Examiner* — Brian T Gedeon
(74) *Attorney, Agent, or Firm* — McDonnell Boehnen Hulbert & Berghoff LLP

(57) ABSTRACT

An electronic system for estimating a subject's blood pressure, comprising a feature extraction module configured for receiving a subject's photoplethysmogram signal, detecting a plurality of signal characteristic points on the received photoplethysmogram signal, calculating a plurality of distances in both time and amplitude between any two of the detected photoplethysmogram signal characteristic points, and providing a feature information signal comprising information about the calculated distances; and a blood pressure calculation module configured for receiving the photoplethysmogram signal, the feature information signal and anthropometric characteristics of the subject, and calculating systolic, diastolic and continuous mean blood pressure values of the subject.

18 Claims, 8 Drawing Sheets

(56) References Cited

OTHER PUBLICATIONS

Zheng, Yali et al., "Wearable Cuff-Less PTT-Based System for Overnight Blood Pressure Monitoring", 35th Annual International Conference of the IEEE EMBS, Osaka, Japan, Jul. 3-7, 2013, pp. 6103-6106.

Zhang, Qiao et al., "Pulse Transit Time-Based Blood Pressure Estimation Using Hilbert-Huang Transform", 31st Annual International Conference of the IEEE EMBS, Minneapolis, Minnesota, Sep. 2-6, 2009, pp. 1785-1788.

Salvi, P., "Pulse Wave Analysis", Pulse Waves, Chapter 6, 2012, pp. 69-87.

\* cited by examiner

SYSTEM AND METHOD FOR BLOOD PRESSURE ESTIMATION

CROSS-REFERENCE TO RELATED APPLICATIONS

The present application is a non-provisional patent application claiming priority to European Patent Application No. 14197973.2 filed Dec. 15, 2014, the contents of which are hereby incorporated by reference.

FIELD OF THE DISCLOSURE

The present description relates generally to electronic systems for arterial blood pressure estimation and more specifically to an electronic system, device and method for non-invasive, cuffless blood pressure estimation.

BACKGROUND

Continuous and non-invasive estimation of arterial blood pressure (BP) without using a cuff has gained emerging interest for health care applications. Instead of commonly used cuff-based measurements, changes in the Pulse Wave Velocity (PWV), i.e., the speed of a pressure pulse propagating along the arterial wall, can be an alternative approach for a continuous, non-invasive and indirect BP measurement, as for example described in "*Continuous blood pressure measurement by using the pulse transit time: comparison to a cuff-based method*", by H. Gesche et al., European Journal of Applied Physiology, vol. 112, no. 1, pp. 309-315, 2012, Springer-Verlag. PWV depends both on the arterial pressure and the intrinsic elastic properties of the arterial wall. Although this relationship is very well defined in a theoretical framework, it is practically difficult to have an accurate estimate of the relationship between PWV and BP since external factors like ageing with its related diseases, cardiovascular risk factors and others can significantly influence arterial wall stiffness.

As a surrogate of PWV, an indirect estimation of BP can be also obtained with the use of Pulse Transit Time (PTT), i.e., the time delay between the R-wave of the ECG and the arrival of the pulse wave measured in a peripheral position, as for example described in "*Wearable Cuff-less PTT-based System for Overnight Blood Pressure Monitoring*", by Yali Zheng et al., Engineering in Medicine and Biology Society (EMBS), 35th Annual International Conference of the IEEE EMBS, pp. 6103-6106, Osaka 3-7 Jul. 2013.

There is a motivation to improve current state of the art electronic systems and methods for non-invasive, cuffless blood pressure estimation.

SUMMARY

A new and improved system and method for non-invasive, cuffless blood pressure estimation is herein proposed, which calculates the systolic, diastolic and/or continuous mean arterial blood pressure of a living being subject.

Example methods and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. In the following detailed description, reference is made to the accompanying figures, which form a part thereof. In the figures, similar symbols typically identify similar components, unless context dictates otherwise. Other embodiments may be utilized, and other changes may be made, without departing from the spirit or scope of the subject matter presented herein.

The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

According to an exemplary embodiment, the system is able to calculate the arterial blood pressure of the subject over time, by gathering data about the subject's variations in blood volume. Such systems may be able to monitor the blood pressure level continuously during a certain lifetime period of the subject in a non-invasively manner and without affecting the daily normal activities of that living being subject.

According to an exemplary embodiment, there is provided a an electronic system for estimating a subject's blood pressure, comprising: a feature extraction module configured for receiving a subject's photoplethysmogram signal, detecting a plurality of signal characteristic points on the received photoplethysmogram signal, calculating a plurality of distances in both time and amplitude between any two of the detected photoplethysmogram signal characteristic points, and providing a feature information signal comprising information about the calculated distances; and a blood pressure calculation module configured for receiving the photoplethysmogram signal, the feature information signal and anthropometric characteristics of the subject, and the blood pressure calculation module comprising a first estimation module configured for calculating systolic and diastolic blood pressure values of the subject based on the received feature information signal and anthropometric characteristics, and a second estimation module configured for calculating continuous mean blood pressure values of the subject based on the calculated systolic and diastolic blood pressure values and the photoplethysmogram signal; and wherein the first estimation module uses a machine-learning regression model for calculating the systolic and diastolic blood pressure values and the second estimation module uses a Hilbert-Huang transform and an empirical mode decomposition process for calculating the continuous mean blood pressure values.

According to an exemplary embodiment, the feature extraction module is further configured generate at least one probabilistic distribution of the calculated distances and provide this information, as a feature information signal, to the blood pressure calculation module.

According to an exemplary embodiment, the first estimation module is trained using mathematical models that, from examples of photoplethysmogram signals, anthropometric characteristics and systolic and diastolic blood pressure values from a plurality of subjects, learn the association between the feature vectors computed in the feature extraction module and the corresponding systolic and diastolic blood pressure values.

According to an exemplary embodiment, the feature extraction module is further configured for receiving a subject's electrocardiogram signal, detecting a plurality of signal characteristic point on the received electrocardiogram signal, calculating a plurality of distances in both time and amplitude between any two of the detected electrocardiogram signal characteristic points and between any point of the detected electrocardiogram signal characteristic points and any point of the photoplethysmogram signal characteristic points, and providing a feature information signal comprising information about the calculated distances; and the first estimation module is further configured for using mathematical models that express the relation between the summarized characteristic point distances of the electrocardiogram signal, the photoplethysmogram signal and a combination of both, the anthropometric characteristics and the arterial blood pressure levels of the subject.

According to an exemplary embodiment, the first estimation module is trained using a linear and/or multiple linear regression model, a random forest regression model, a Bayesian model and/or general machine learning regression model.

According to an exemplary embodiment, the machine-learning regression model is a discretized version of a regression model.

According to an exemplary embodiment, the regression module is trained using a linear and/or multiple linear classification and regression model, a random forest classification and regression model, a Bayesian model and/or general machine learning-based classification and regression model.

The description also relates to an electronic device comprising a system for estimating a subject's blood pressure according to embodiments herein described.

The description also relates to a method for estimating a subject's blood pressure comprising: receiving a subject's photoplethysmogram signal and anthropometric characteristics; detecting a plurality of signal characteristic points on the received photoplethysmogram signal; calculating a plurality of distances in both time and amplitude between any two of the detected photoplethysmogram signal characteristic points; calculating, based on the calculated distances and the anthropometric characteristics, the subject's systolic and diastolic blood pressure values using a machine-learning regression model; and calculating, based on the received systolic and diastolic blood pressure values and photoplethysmogram signal, the subject's continuous mean blood pressure values using a Hilbert-Huang transform and an empirical mode decomposition process.

According to an exemplary embodiment, the method further comprises receiving a subject's electrocardiogram signal; detecting a plurality of signal characteristic points on the received electrocardiogram signal; and calculating a plurality of distances in both time and amplitude between any two of the detected electrocardiogram signal characteristic points and between any of the detected electrocardiogram signal characteristic points and any of the photoplethysmogram signal characteristic points.

The description also relates to a computer program product comprising computer program code means adapted to calculate a subject's blood pressure according to the methods herein described when the program is run on a computer, and to a computer readable storage medium comprising such computer program.

According to an exemplary embodiment, there is provided a system for estimating a subject's blood pressure, comprising a feature extraction module configured for receiving a subject's photoplethysmogram (PPG) signal, detect a plurality of signal characteristic points on the received PPG signal, calculate a plurality of possible pair-wise distances in both time and amplitude between the detected PPG signal characteristic points, and providing a feature information signal comprising information about the calculated distances; and a blood pressure calculation module configured for receiving the PPG signal, the feature information signal and anthropometric characteristics of that subject; and the blood pressure calculation module comprising a regression module configured for calculating the subject's systolic and diastolic blood pressure values using a machine-learning regression model and based on the received feature information signal and anthropometric characteristics; and an empirical mode decomposition module configured for calculating the subject's continuous mean blood pressure values using a Hilbert-Huang transform and an empirical mode decomposition process and based on the received systolic and diastolic blood pressure values and PPG signal.

According to an exemplary embodiment, the feature extraction module may be further configured generate at least one probabilistic distribution of the calculated distances and provide this information, as a feature information signal, to the blood pressure calculation module.

According to an exemplary embodiment, the regression module is trained using mathematical models that, from examples of PPG signals, anthropometric characteristics and systolic and diastolic blood pressure from a plurality of subjects, learn the association between the feature vectors computed in the feature extraction module and the corresponding systolic and diastolic blood pressure values.

According to an exemplary embodiment, the empirical mode decomposition module uses the subject's systolic and diastolic blood pressure values provided by the regression module for shifting the continuous mean blood pressure values to the correct levels of blood pressure.

According to an exemplary embodiment, the feature extraction module is further configured for receiving a subject's electrocardiogram (ECG) signal, detect a plurality of signal characteristic points on the received ECG signal, calculate a plurality of possible pair-wise distances in both time and amplitude between the detected electrocardiogram signal characteristic points and between the detected ECG signal characteristic points and the PPG signal characteristic points, and providing a feature information signal comprising information about the calculated distances; and the regression module is further configured for using mathematical models that express the relation between the summarized characteristic point distances of the ECG signal, the PPG signal and a combination of both ECG and PPG the anthropometric characteristics and the arterial blood pressure levels of the subject.

According to an exemplary embodiment, the regression module is trained using a linear and/or multiple linear regression model, a random forest regression model, a Bayesian model and/or general machine learning regression model.

According to an exemplary embodiment, there is provided a method for estimating a subject's blood pressure comprising: receiving a subject's PPG signal and anthropometric characteristics; detecting a plurality of signal characteristic points on the received PPG signal; calculating a plurality of possible pair-wise distances in both time and amplitude between the detected PPG signal characteristic points, calculating the subject's systolic and diastolic blood pressure values using a machine-learning regression model and based on the calculated distances and the anthropometric characteristics; and calculating the subject's continuous mean blood pressure values using a Hilbert-Huang transform and an empirical mode decomposition process and based on the received systolic and diastolic blood pressure values and PPG signal.

According to an exemplary embodiment, the method for estimating a subject's blood pressure further comprises:

receiving the subject's ECG signal; detecting a plurality of signal characteristic points on the received ECG signal; calculating a plurality of possible pair-wise distances in both time and amplitude between the detected ECG signal characteristic points and between the detected ECG signal characteristic points and the PPG signal characteristic points.

BRIEF DESCRIPTION OF THE FIGURES

The above and other aspects of the system and method according to the present description will be shown and explained with reference to the non-restrictive example embodiments described hereinafter.

DETAILED DESCRIPTION

In the following, in the description of exemplary embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the main claim. Furthermore, combinations of features of different embodiments are meant to be within the scope of the invention, as would be clearly understood by those skilled in the art. Additionally, in other instances, well-known methods, structures and techniques have not been shown in detail in order not to obscure the conciseness of the description.

Figure 1:
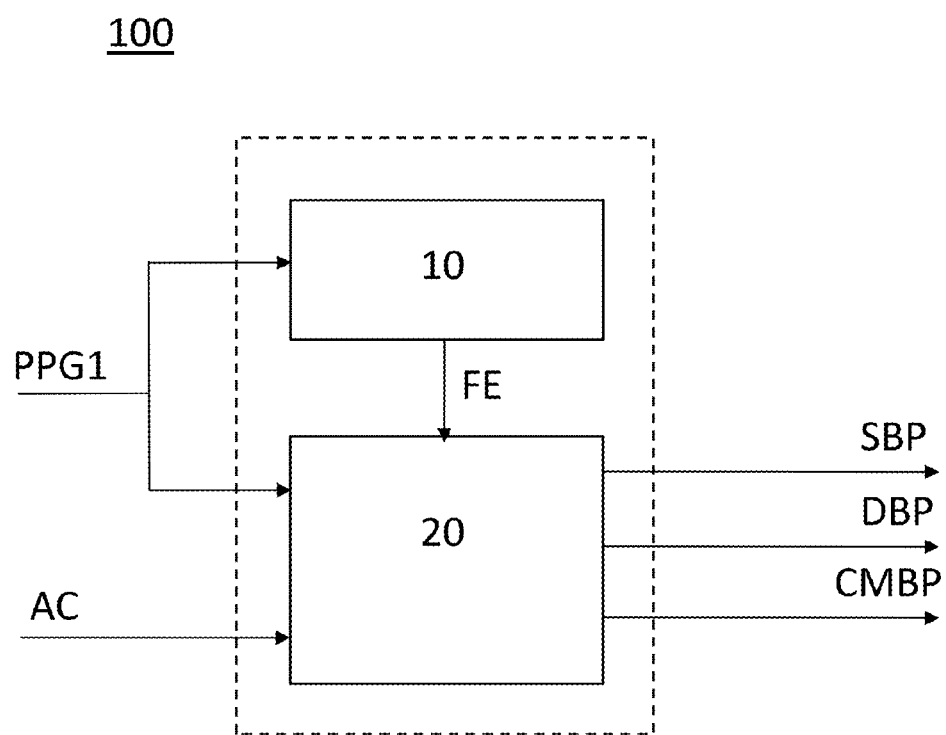
FIG. 1 shows a first general block diagram of an exemplary system for blood pressure estimation.

FIG. 1 shows a first general block diagram of an exemplary electronic system 100 for arterial blood pressure estimation, comprising a feature extraction module 10 and a blood pressure calculation module 20. The feature extraction module 10 receives a PPG signal PPG1 and generates a feature information signal FE. The blood pressure calculation module 20 receives the PPG signal PPG1, the feature information signal FE and an anthropometric characteristics information signal AC and generates a systolic blood pressure information signal SBP, a diastolic blood pressure information signal DBP and a continuous mean blood pressure information signal CMBP.

According to an exemplary embodiment, the anthropometric characteristics information signal AC is a signal comprising information about the subject's age, weight and/or height. This information may be input by a subject, received from another electronic device or module and/or already stored in the system.

According to an exemplary embodiment, the blood pressure calculation module 20 is configured to calculate a systolic, diastolic and/or a mean continuous arterial blood pressure of a living being subject based on a PPG signal PPG1, a feature information signal FE comprising statistics of the distribution of characteristic points of the PPG signal PPG1 and anthropometric characteristics AC of that subject.

Figure 2:
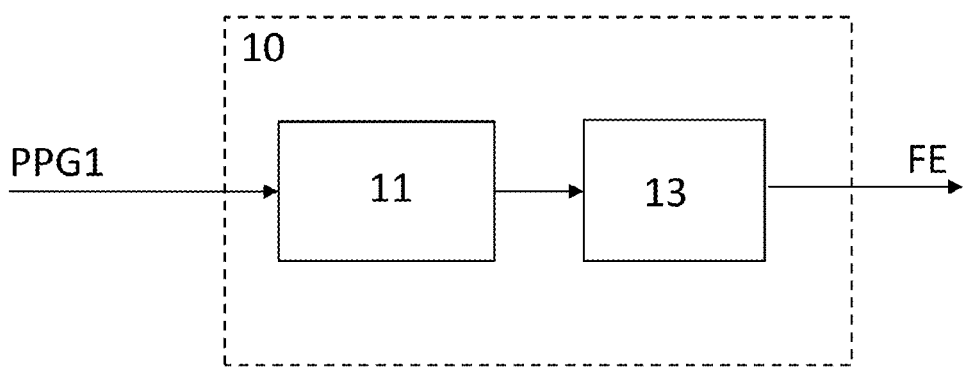
FIG. 2 shows a first block diagram of a feature extraction module according to an exemplary embodiment.
Figure 3:
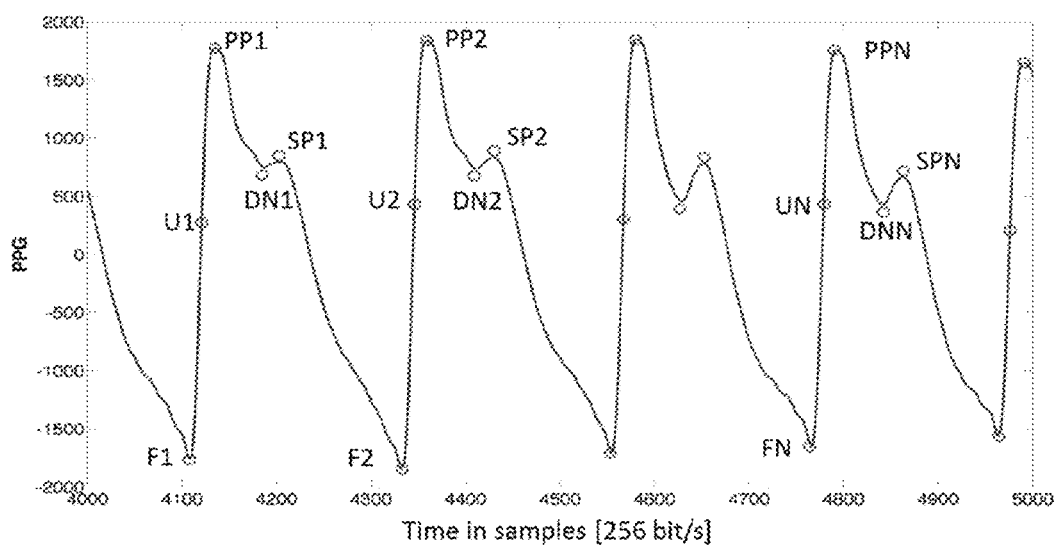
FIG. 3 shows a PPG signal window in which a plurality of characteristic points are detected according to an exemplary embodiment.

FIG. 2 shows a first exemplary block diagram of a feature extraction module 10 according to an embodiment. The feature extraction module 10 comprises a PPG point detection module 11 and a distance computation module 13. According to an exemplary embodiment, the PPG point detection module 11 receives as input the PPG signal PPG1, which may be, for example, the output from a pulseoximeter sensor and which may be received over a hardwired or wireless connection. The PPG signal PPG1 may also be filtered before being received by the feature extraction module 10. According to an exemplary embodiment, a certain time window or segment, e.g., 5 seconds, of the received PPG signal or data is collected and temporarily stored in the module, and then the PPG point detection module 11 performs, on that stored PPG signal, a detection of a plurality of PPG signal characteristic points, such as and not limited to, a foot F1, an upstroke U1, a primary peak PP1, a dicrotic notch DN1 and/or a secondary peak SP1, as shown in FIG. 3. According to an exemplary embodiment, the PPG point detection module 11 may compute characteristic points on the first and second derivative of the PPG signal.

According to an exemplary embodiment, the detected PPG characteristic points are then provided to the distance computation module 13 in the form of, for example two-dimensional vectors, in which for example, the first coordinate represents the timestamp and the second coordinate represents the amplitude of the detected points. The distance computation module 13 then calculates a plurality of or all the possible pair-wise distances (in both time and in amplitude) between some or all the coordinates of the received two-dimensional vectors, that is, the distance or difference in time and/or amplitude between any two detected characteristic points. According to an exemplary embodiment, the distance computation module 13 may calculate distances between normalized amplitudes of the PPG signal. The calculated distances are then provided, as a feature information signal FE, to the blood pressure calculation module 20. According to an exemplary embodiment, the distance computation module 13 may further determine statistics of the distribution of such PPG characteristic points and distances and provide at least one probabilistic distribution of the computed distances, such as, but not limited to, one or more histograms, as a feature information signal FE to the blood pressure calculation module 20. According to an embodiment, based on the same distribution, it is possible to compute several histograms based on the width of bins.

Those distributions may be aggregated in a final feature vector representing the input to the blood pressure calculation module 20.

Figure 4:
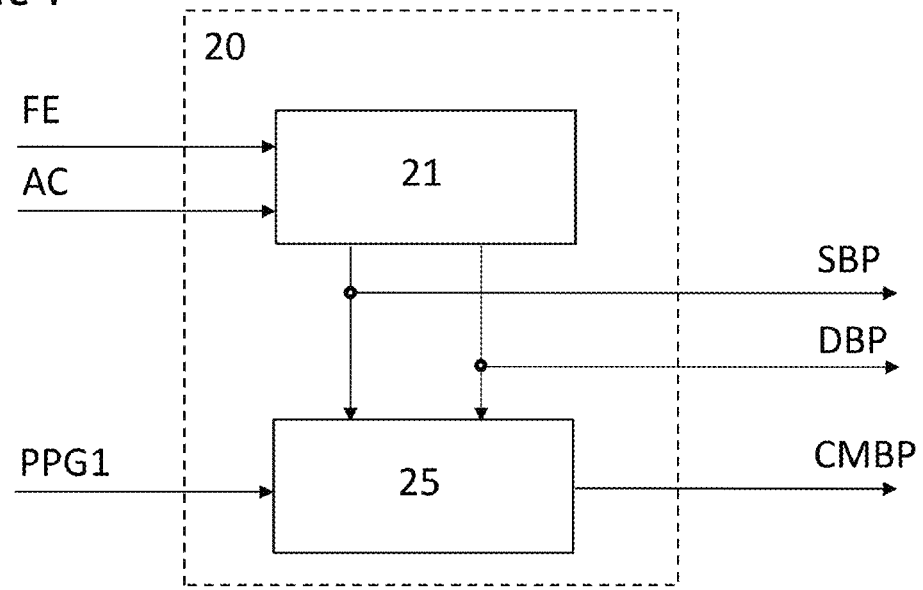
FIG. 4 shows an exemplary block diagram of a blood pressure calculation module according to an exemplary embodiment.

FIG. 4 shows an exemplary block diagram of a blood pressure calculation module 20 according to an embodiment. The blood pressure calculation module 20 comprises a first estimation module 21 and a second estimation module 25. According to an exemplary embodiment, the first estimation module 21 is a machine-learning based regression module that receives the feature information signal FE and the anthropometric characteristics information signal AC and calculates an estimation of the subject' systolic blood pressure SBP and diastolic blood pressure DBP.

According to an exemplary embodiment, the first estimation module 21 is trained using mathematical models that, from examples of PPG signals, anthropometric characteristics and systolic and diastolic blood pressure, learn the association between the feature vectors computed in the feature extraction module 10 and the corresponding systolic and diastolic blood pressure values. Examples of such mathematical models may be, but are not limited to, linear and/or multiple linear regression models, random forest regression models, Bayesian models and/or general machine learning regression models. According to an exemplary embodiment, the parameters of the regression models may be derived using information about statistics of the distance computed by the feature extraction module 10 and arterial blood pressure reference values from a plurality of subjects. The mathematical models express the relation between the summarized distances between characteristic points of a PPG signal, the anthropometric characteristics and the arterial blood pressure levels of the subject.

According to an exemplary embodiment the first estimation module 21 is a machine-learning based classification and regression module that receives the feature information signal FE and the anthropometric characteristics information signal AC and calculates an estimation of the subject' systolic blood pressure SBP and diastolic blood pressure DBP. The first estimation model 21 may use linear and/or multiple linear classification and regression models, random forest classification and regression models, Bayesian models and/or general machine learning classification and regression models. According to an exemplary embodiment, the parameters of the classification and regression models may be derived using information about statistics of the distance computed by the feature extraction module 10 and arterial blood pressure reference values from a plurality of subjects. It shall be noted that a classification and regression model is a discretized version of a regression model, which may provide an estimation of the subject' systolic and diastolic blood pressure in some applications.

According to an exemplary embodiment, the second estimation module 25 receives as input the PPG signal PPG1, the systolic blood pressure information signal SBP and the diastolic blood pressure information signal DBP and calculates an estimation of the subject's continuous mean blood pressure CMBP. According to an exemplary embodiment, the second estimation module 25 is based on the Hilbert-Huang transform (HHT) and Empirical Mode Decomposition (EMD), wherein the EMD is used for the estimation of the continuous mean arterial blood pressure CMBP from the PPG signal. According to an exemplary embodiment, the second estimation module 25 uses the systolic blood pressure information signal SBP and the diastolic blood pressure information signal DBP provided by the first estimation module 21 for shifting the output of the EMD process (the continuous mean arterial blood pressure CMBP values) to the correct levels of blood pressure. This can be done for example by shifting the calculated continuous mean arterial blood pressure values using a mean arterial pressure baseline. The Mean Arterial Pressure value baseline can be calculated according to the formula:

$$\text{Mean Arterial Pressure} = DBP + \frac{SBP - BDP}{3}$$

as described in document "*How Vascular Hemodynamics Affects Blood Pressure*" by Salvi, P., Pulse Waves, XII, p. 138, 2012.

As it is known in the art, the HHT provides a method of analysing nonstationary and nonlinear time series data. It uses the EMD method to decompose a signal into so-called intrinsic mode functions. For example, in document "*Pulse transit time-based blood pressure estimation using hilbert-huang transform*", by Zhang et al., Engineering in Medicine and Biology Society, 31st Annual International Conference of the IEEE EMBS, pp. 1785-1788, 3-6 Sep. 2009, the authors use HHT and EMD for ECG and PPG conditioning before the computation of the Pulse Transit Time (PTT), i.e. they apply EMD for denoising both ECG and PPG and they use the denoised signals for computing a more accurate PTT.

Figure 5:
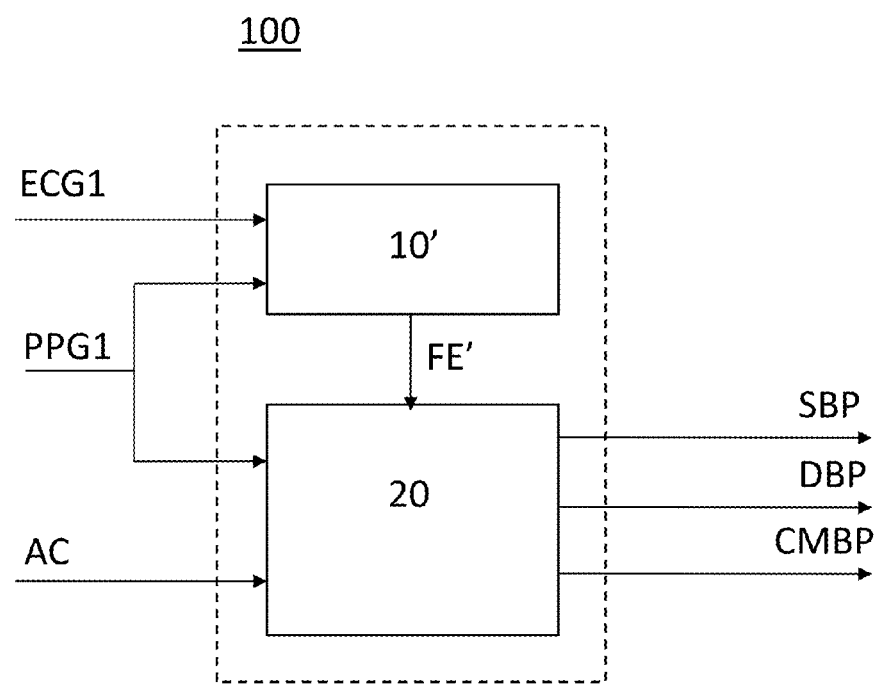
FIG. 5 shows a second general block diagram of an exemplary system for blood pressure estimation.

FIG. 5 shows a second general block diagram of an exemplary electronic system 100 for arterial blood pressure estimation, comprising a feature extraction module 10' and a blood pressure calculation module 20. The feature extraction module 10' receives both a PPG signal PPG1 and an ECG signal ECG1 and generates a feature information signal FE'. The blood pressure calculation module 20 receives the PPG signal PPG1, the feature information signal FE' and an anthropometric characteristics information signal AC and generates a systolic blood pressure information signal SBP, a diastolic blood pressure information signal DBP and a continuous mean blood pressure information signal CMBP.

According to an exemplary embodiment, the anthropometric characteristics information signal AC is a signal comprising information about the subject's age, weight and/or height. This information may be input by a subject, received from another device or module and/or already stored in the system.

According to an exemplary embodiment, the blood pressure calculation module 20 is configured to calculate a systolic, diastolic and/or a mean continuous arterial blood pressure of a living being subject based on a PPG signal PPG1, a feature information signal FE' comprising statistics of the distribution of characteristic points of the PPG signal PPG1, an ECG signal ECG1 and anthropometric characteristics AC of that subject.

Figure 6:
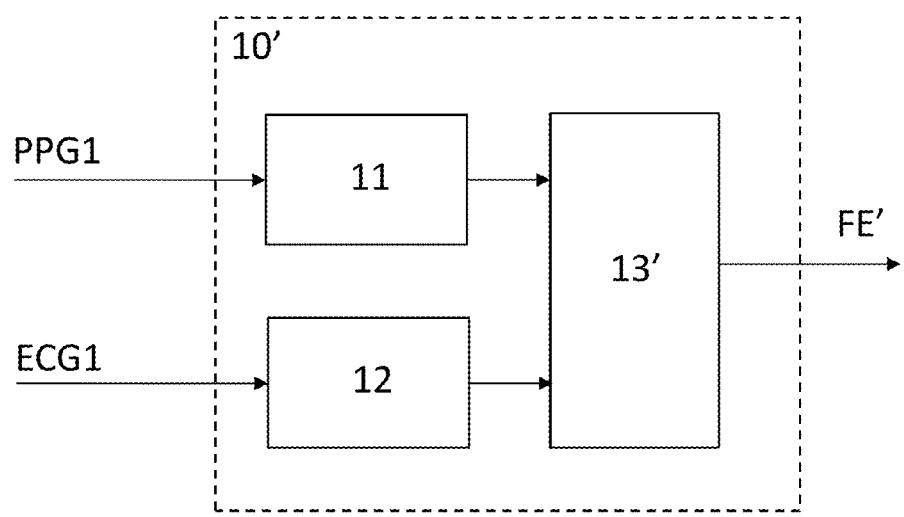
FIG. 6 shows a second block diagram of a feature extraction module according to an exemplary embodiment.

FIG. 6 shows a second exemplary block diagram of a feature extraction module 10' according to an embodiment. The feature extraction module 10' comprises a PPG point detection module 11, an ECG point detection module 12 and a distance computation module 13'.

According to an exemplary embodiment, the PPG point detection module 11 receives as input the PPG signal PPG1, which may be, for example, the output from a pulseoximeter sensor and may be received over a hardwired or wireless connection. The PPG signal PPG1 may also be filtered before being received by the feature extraction module 10'. According to an exemplary embodiment, a certain time window or segment, e.g., 5 seconds, of the received PPG signal or data is collected and temporarily stored in the module, and then the PPG point detection module 11 performs, on that stored PPG signal, a detection of a plurality of PPG signal characteristic points, such as and not limited to, a foot F1, an upstroke U1, a primary peak PP1, a dicrotic notch DN1 and/or a secondary peak SP1, as for example shown in FIG. 3. According to an exemplary embodiment, the PPG point detection module 11 may detect characteristic points on the first and second derivative of the PPG signal.

Figure 7:
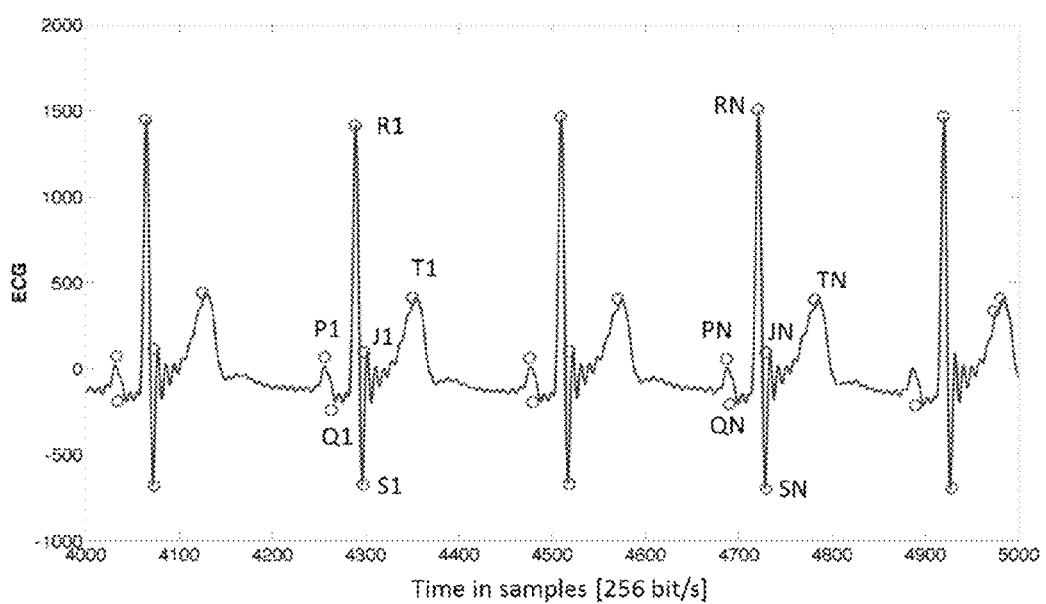
FIG. 7 shows an ECG signal window in which a plurality of characteristic points are detected according to an exemplary embodiment.

According to an exemplary embodiment, the ECG point detection module 12 receives as input the ECG signal ECG1, which may be, for example, the output from an ECG sensor and may be received over a hardwired or wireless connection. The ECG signal ECG1 may also be filtered before being received by the feature extraction module 10'. According to an exemplary embodiment, a certain time window or segment, e.g., 5 seconds, of the received ECG signal or data is collected and temporarily stored in the module, and then the ECG point detection module 12 performs, on that stored ECG signal, a detection of a plurality of ECG signal characteristic points, such as and not limited to, a P1, Q1, R1, S1 and/or T1 peaks of the cardiac cycles, as shown in FIG. 7. According to an exemplary embodiment, the ECG point detection module 12 may compute characteristic points on the first and second derivative of the ECG signal.

According to an exemplary embodiment, the detected PPG and ECG characteristic points are then provided to the distance computation module 13', each in the form of, for example, two-dimensional vectors, in which for example, the first coordinate represents the timestamp and the second coordinate the amplitude of the detected points. The distance computation module 13' then calculates some or all the possible pair-wise distances (in both time and in amplitude) between some or all the coordinates of the received two-dimensional vectors for the PPG and ECG signal individually and between the ECG and PPG signals. According to an exemplary embodiment, the distance computation module 13' may calculate distances between normalized amplitudes of the PPG and ECG signals. The calculated distances are then provided, as a feature information signal FE', to the blood pressure calculation module 20. According to an exemplary embodiment, the distance computation module 13' may provide at least three probabilistic distributions of all the computed distances (at least one for the ECG, one for the PPG and one for the distances between the ECG and PPG coordinates), such as, but not limited to, a histogram, as a feature information signal FE' to the blood pressure calculation module 20. According to an exemplary embodiment, those at least three probabilistic distributions may be also aggregated in a final feature vector representing the input to the blood pressure calculation module 20.

It shall be noted then that, according to an exemplary embodiment, the blood pressure calculation module 20 may further take in consideration the additional ECG information in order to improve the calculation of the systolic blood pressure SBP, the diastolic blood pressure DBP and/or the continuous mean blood pressure CMBP. For example, according to an exemplary embodiment, the first estimation module 21 is trained using mathematical models that, from examples of ECG and PPG signals, anthropometric characteristics and systolic and diastolic blood pressure, learn the association between the feature vectors computed in the feature extraction module 10' and the corresponding systolic and diastolic blood pressure values. The mathematical models of the first estimation module 21 may express the relation between the summarized distances between characteristic points of ECG, PPG and a combination of both (relationship between the ECG characteristic points and the PPG characteristic points), the anthropometric characteristics and the arterial blood pressure levels of the subject, e.g., this module may use mathematical models based on information about ECG value distribution, PPG value distributions, a combination of both and anthropometric characteristics of the subject. Examples of such mathematical models may be, but are not limited to, linear and/or multiple linear regression models, random forest regression models, Bayesian models and/or general machine learning regression models. According to an exemplary embodiment, the parameters of the regression models may be derived using information about statistics of the distance computed by the feature extraction module 10' and arterial blood pressure reference values from a plurality of subjects. According to an embodiment, the regression model may be a discretized version of a regression model and examples of such used models may comprise linear and/or multiple linear classification and regression models, random forest classification and regression models, Bayesian models and/or general machine learning classification and regression models. The parameters of the classification and regression models may be derived using information about statistics of the distance computed by the feature extraction module 10' and arterial blood pressure reference values from a plurality of subjects. The second estimation module 25 may use non-stationary and non-linear adaptive time-domain methods. Example of such methods may be the use of a Hilbert-Huang Transform to provide a continuous estimation of the mean arterial blood pressure of the subject. The systolic and diastolic blood pressure estimation values provided by the first estimation module 21 may be used by the second estimation module 25 for shifting the output of the EMD process (the continuous mean arterial blood pressure CMBP values) to the correct blood pressure values using a mean arterial pressure baseline value as is known in the art.

Figure 8:
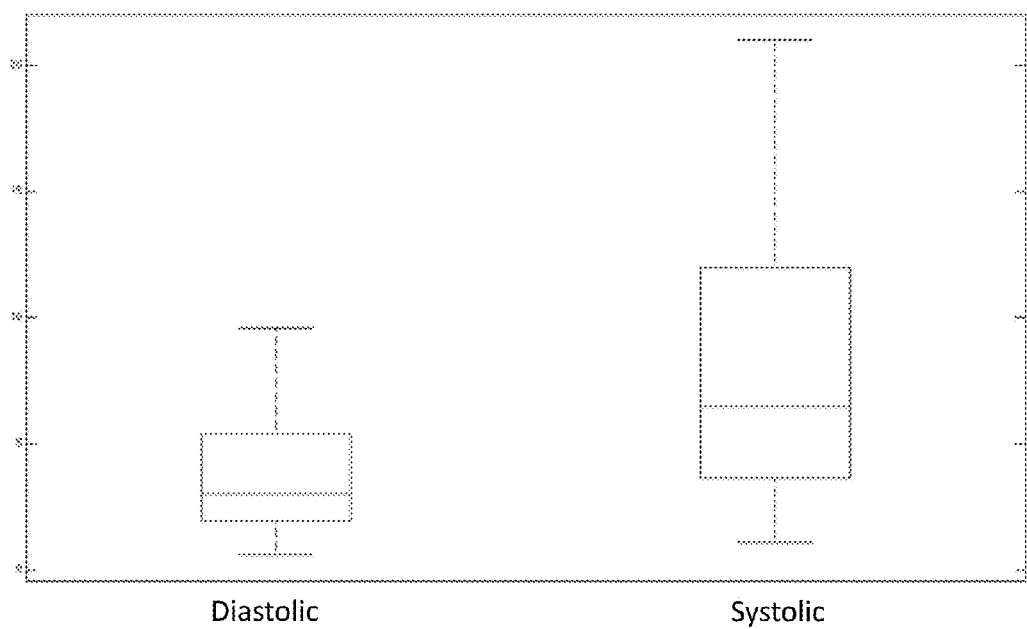
FIG. 8 shows an exemplary graph of the absolute mean error for diastolic and systolic blood pressure values calculated according to an exemplary embodiment of the present disclosure and in comparison to values measured by a blood pressure estimation reference device.

FIG. 8 shows an example of the absolute mean error in diastolic and systolic blood pressure values calculated with a reference Continuous Noninvasive Arterial Pressure (CNAP) device and with a system according to an exemplary embodiment of the present disclosure. The models used in the system according to an exemplary embodiment of the present disclosure were derived from data of 20 subjects. The average absolute error is lower than 7 mmHg and complies with standard testing protocol requirements.

Figure 9:
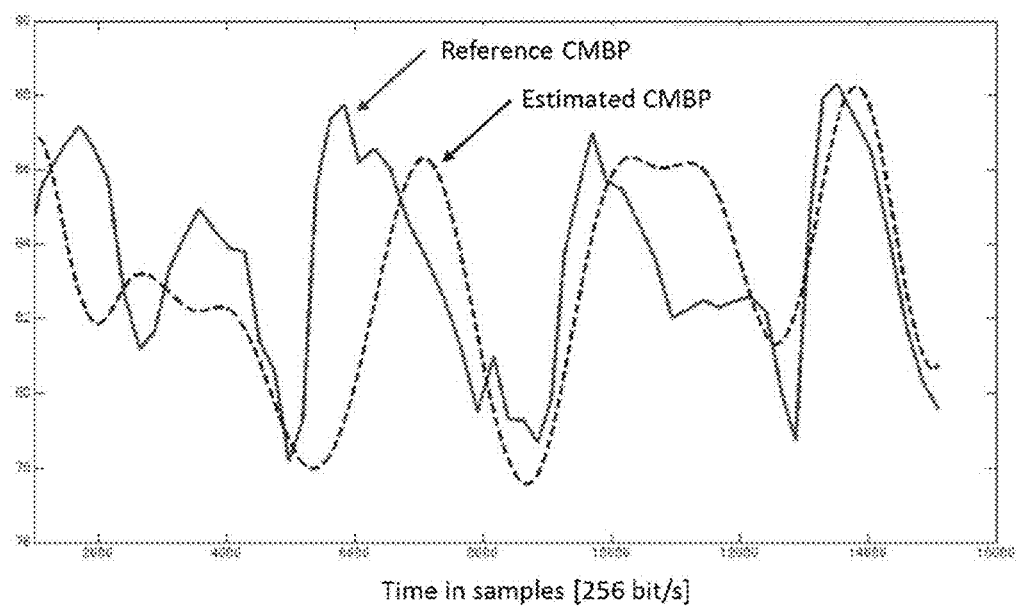
FIG. 9 shows an exemplary graph of estimated continuous mean blood pressure signal values calculated according to an exemplary embodiment of the present disclosure and in comparison to signal values measured by a blood pressure estimation reference device.

FIG. 9 shows an exemplary comparison graph illustrating the continuous mean blood pressure signal values provided by a reference CNAP device and the continuous mean blood pressure signal values estimated using a method according to an exemplary embodiment of the present disclosure. The models used in the system according to an exemplary embodiment of the present disclosure were derived from data of 20 subjects. Results obtained show a correlation coefficient of 0.83 for all subjects.

It shall be noted that the system 100 for blood pressure estimation according to embodiments of the present disclosure may be implemented according to hardware and/or software state of the art techniques, comprising for example a microprocessor, a controller, a microcontroller, and/or a digital signal processor that can understand and execute software program instructions. Some programmable hardware logic and memory means may be specifically designed also for executing the method or parts of it according to exemplary embodiments. It shall be also understood that although, for simplicity, the exemplary embodiments described herein comprise system operations, calculations and methods applied to and during a certain time window or segment of the received signals, the time windows may vary in length and the system operations, calculations and methods herein described may be applied to a plurality of the time windows of the received signals; the time window length and the number and selection of signal time windows being a design choice.

Figure 10:
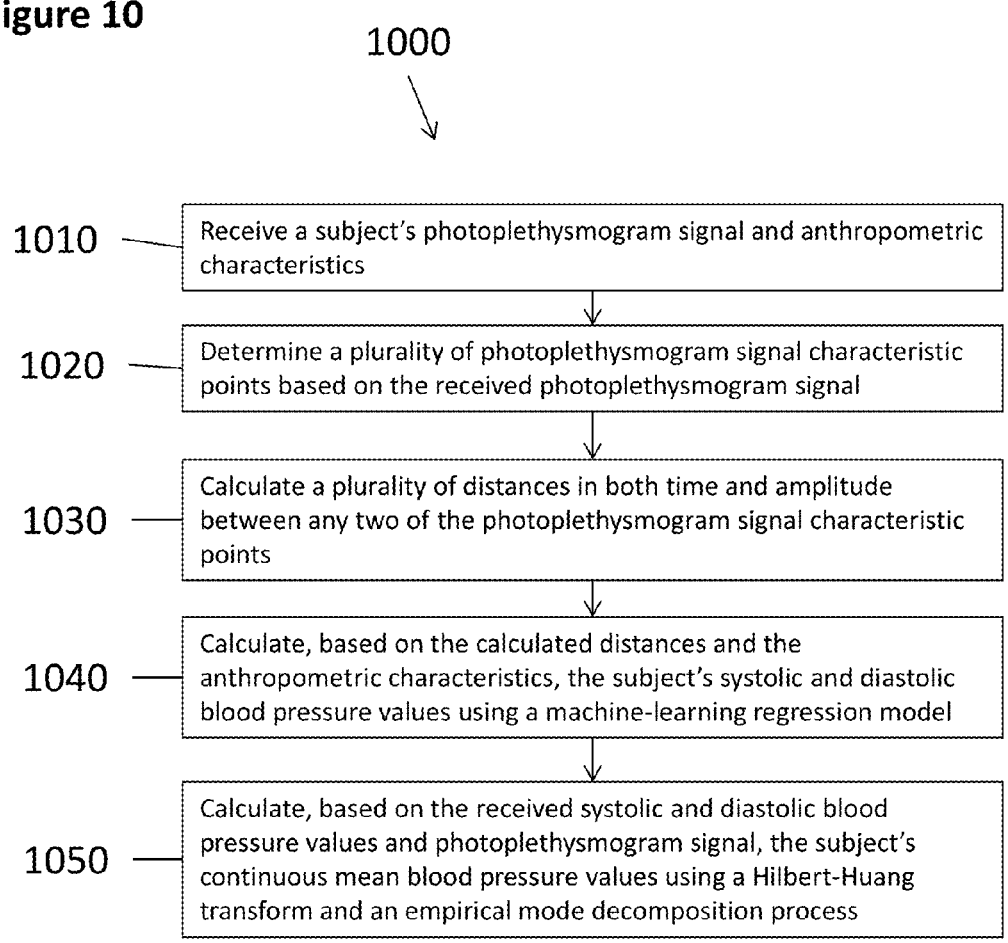
FIG. 10 shows a flowchart of a method according to an exemplary embodiment.

FIG. 10 shows a flowchart of a method 1000 according to an exemplary embodiment. The method 1000 may include various blocks or steps. The blocks or steps may be carried out individually or in combination. The blocks or steps may be carried out in any order and/or in series or in parallel. Further, blocks or steps may be omitted or added to method 1000.

Some or all blocks of method 1000 may be carried out by system 100 as illustrated and described in reference to FIGS. 1-9. For example, some or all blocks of method 1000 may be carried out by a controller of system 100. The controller may include some or all of the feature extraction module 10 and/or the blood pressure calculation module 20. Additionally or alternatively, at least some portions of the controller may be external to the system 100. The controller may include a memory, e.g., a non-transitory computer readable medium, and at least one processor configured to execute instructions stored in the memory so as to carry out various operations.

Block 1010 includes receiving a subject's photoplethysmogram signal and anthropometric characteristics.

Block 1020 includes determining or detecting a plurality of photoplethysmogram signal characteristic points based on the received photoplethysmogram signal.

Block 1030 includes calculating a plurality of distances in both time and amplitude between any two of the photoplethysmogram signal characteristic points.

Block 1040 includes calculating, based on the calculated distances and the anthropometric characteristics, the subject's systolic and diastolic blood pressure values using a machine-learning regression model.

Block 1050 includes calculating, based on the received systolic and diastolic blood pressure values and photoplethysmogram signal, the subject's continuous mean blood pressure values using a Hilbert-Huang transform and an empirical mode decomposition process.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Figure 11:
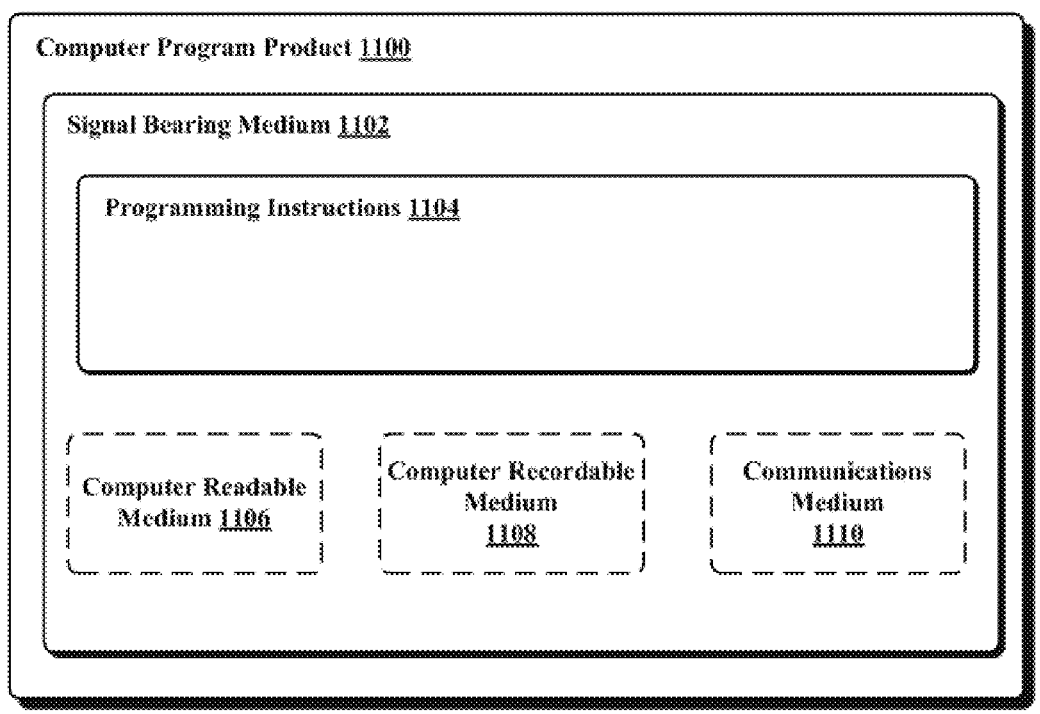
FIG. 11 shows a schematic drawing of a computer program product according to an exemplary embodiment.

FIG. 11 shows a schematic drawing of a computer program product 1100 according to an exemplary embodiment. In one embodiment, the example computer program product 1100 is provided using a signal bearing medium 1102. The signal bearing medium 1102 may include one or more programming instructions 1104 that, when executed by one or more processors may provide functionality or portions of the functionality described above with respect to FIGS. 1-10. In some examples, the signal bearing medium 1102 can be a computer-readable medium 1106, such as, but not limited to, a hard disk drive, a Compact Disc (CD), a Digital Video Disk (DVD), a digital tape, memory, etc. In some implementations, the signal bearing medium 1102 can be a computer recordable medium 1108, such as, but not limited to, memory, read/write (R/W) CDs, R/W DVDs, etc. In some implementations, the signal bearing medium 1102 can be a communications medium 1110, such as, but not limited to, a digital and/or an analog communication medium (e.g., a fiber optic cable, a waveguide, a wired communications link, a wireless communication link, etc.). Thus, for example, the signal bearing medium 1102 can be conveyed by a wireless form of the communications medium 1110.

The one or more programming instructions 1104 can be, for example, computer executable and/or logic implemented instructions. In some examples, a computing device such as a controller, the feature extraction module 10, and/or the blood pressure calculation module 20 of FIG. 1 may be configured to provide various operations, functions, or actions in response to the programming instructions 1104 conveyed to controller, the feature extraction module 10, and/or the blood pressure calculation module 20 by one or more of the computer readable medium 1106, the computer recordable medium 1108, and/or the communications medium 1110.

What is claimed is:

1. An electronic system configured to estimate a subject's blood pressure, comprising:
    a feature extraction module configured to receive a subject's photoplethysmogram signal, detect a plurality of signal characteristic points on the received photoplethysmogram signal, calculate a plurality of distances in both time and amplitude between any two of the detected photoplethysmogram signal characteristic points, and provide a feature information signal comprising information about the calculated distances; and
    a blood pressure calculation module configured to receive the photoplethysmogram signal, the feature information signal, and anthropometric characteristics of the subject, wherein the blood pressure calculation module includes:
        a first estimation module configured to calculate systolic and diastolic blood pressure values of the subject based on the received feature information signal and anthropometric characteristics; and
        a second estimation module configured to calculate continuous mean blood pressure values of the subject based on the calculated systolic and diastolic blood pressure values and the photoplethysmogram signal;
        and wherein the first estimation module uses a machine-learning regression model to calculate the systolic and diastolic blood pressure values, and the second estimation module uses a Hilbert-Huang transform and an empirical mode decomposition process to calculate the continuous mean blood pressure values.

2. The electronic system configured to estimate a subject's blood pressure according to claim 1, wherein the feature extraction module is further configured generate at least one probabilistic distribution of the calculated distances and provide this information, as a feature information signal, to the blood pressure calculation module.

3. The electronic system configured to estimate a subject's blood pressure according to claim 1, wherein the plurality of distances are represented as feature vectors, and wherein the first estimation module is trained using mathematical models that, from examples of photoplethysmogram signals, anthropometric characteristics, and systolic and diastolic blood pressure values from a plurality of subjects, learn the association between the feature vectors computed in the feature extraction module and the corresponding systolic and diastolic blood pressure values.

4. The electronic system configured to estimate a subject's blood pressure according to claim 1, wherein the first estimation module is trained using at least one of a linear regression model, a multiple linear regression model, a random forest regression model, a Bayesian model, or a general machine learning regression model.

5. The electronic system configured to estimate a subject's blood pressure according to claim 1, wherein the machine-learning regression model is a discretized version of a regression model.

6. The electronic system configured to estimate a subject's blood pressure according to claim 5, wherein the blood pressure calculation module comprises a regression module, wherein the regression module is trained using at least one of a linear classification and regression model, a multiple linear classification and regression model, a random forest classification and regression model, a Bayesian model, or a general machine learning-based classification and regression model.

7. An electronic device comprising an electronic system for estimating a subject's blood pressure according to claim 1.

8. The electronic system configured to estimate a subject's blood pressure according to claim 1, wherein the signal characteristic points comprise at least one of: a foot, an upstroke, a primary peak, a dicrotic notch, or a secondary peak.

9. A method for estimating a subject's blood pressure comprising:
receiving a subject's photoplethysmogram signal and anthropometric characteristics;
determining a plurality of photoplethysmogram signal characteristic points based on the received photoplethysmogram signal;
calculating a plurality of distances in both time and amplitude between any two of the photoplethysmogram signal characteristic points;
calculating, based on the calculated distances and the anthropometric characteristics, the subject's systolic and diastolic blood pressure values using a machine-learning regression model; and
calculating, based on the received systolic and diastolic blood pressure values and photoplethysmogram signal, the subject's continuous mean blood pressure values using a Hilbert-Huang transform and an empirical mode decomposition process.

10. The method for estimating a subject's blood pressure according to claim 9 further comprising:
receiving a subject's electrocardiogram signal;
determining a plurality of electrocardiogram signal characteristic points based on the received electrocardiogram signal; and
calculating a plurality of distances in both time and amplitude between any two of the electrocardiogram signal characteristic points and between any of the electrocardiogram signal characteristic points and any of the photoplethysmogram signal characteristic points.

11. A non-transitory computer readable medium comprising instructions executable by a computer to carry out operations directed to the method of claim 9.

12. The non-transitory computer readable medium of claim 11, wherein the operations further comprise:
receiving a subject's electrocardiogram signal;
determining a plurality of electrocardiogram signal characteristic points based on the received electrocardiogram signal; and
calculating a plurality of distances in both time and amplitude between any two of the electrocardiogram signal characteristic points and between any of the electrocardiogram signal characteristic points and any of the photoplethysmogram signal characteristic points.

13. The method of claim 9, wherein the signal characteristic points comprise at least one of: a foot, an upstroke, a primary peak, a dicrotic notch, or a secondary peak.

14. A system comprising:
a feature extraction module;
a blood pressure calculation module; and
a controller comprising a memory and at least one processor, wherein the memory is configured to store instructions and wherein the at least one processor is configured to execute the instructions so as to carry out operations, the operations comprising:
receiving, via the feature extraction module, a subject's photoplethysmogram signal;
determining a plurality of photoplethysmogram signal characteristic points based on the received photoplethysmogram signal;
calculating a plurality of distances in both time and amplitude between any two of the detected photoplethysmogram signal characteristic points;
providing a feature information signal comprising information about the calculated distances;
receiving, via the blood pressure calculation module, the photoplethysmogram signal, the feature information signal, and anthropometric characteristics of the subject;
calculating systolic and diastolic blood pressure values of the subject based on the received feature information signal, anthropometric characteristics, and a machine- learning regression model for calculating the systolic and diastolic blood pressure values; and
calculating continuous mean blood pressure values of the subject based on the calculated systolic and diastolic blood pressure values, the photoplethysmogram signal, a Hilbert-Huang transform, and an empirical mode decomposition process for calculating the continuous mean blood pressure values.

15. The system of claim 14, wherein the operations further comprise:
generating, via the feature extraction module, at least one probabilistic distribution of the calculated distances; and
providing the at least one probabilistic distribution of the calculated distances as a feature information signal to the blood pressure calculation module.

16. The system of claim 14, wherein the blood pressure calculation module comprises a first estimation module, wherein the plurality of distances are represented as feature vectors, and wherein the operations further comprise training the first estimation module using mathematical models that, from examples of photoplethysmogram signals, anthropometric characteristics, and systolic and diastolic blood pressure values from a plurality of subjects, learn the association between the feature vectors computed in the feature extraction module and the corresponding systolic and diastolic blood pressure values.

17. The system of claim 14, wherein the machine-learning regression model comprises a discretized version of a regression model.

18. The system of claim 14, wherein the blood pressure calculation module comprises a regression module, wherein the regression module is trained using a linear and/or multiple linear classification and regression model, a random forest classification and regression model, a Bayesian model, or a general machine learning-based classification and regression model.

\* \* \* \* \*